(12) United States Patent
Rahe-Meyer

(10) Patent No.: US 7,955,273 B2
(45) Date of Patent: Jun. 7, 2011

(54) DEVICE FOR VERIFYING AND MONITORING VITAL PARAMETERS OF THE BODY

(76) Inventor: Niels Rahe-Meyer, Hannover (DE)

( * ) Notice: Subject to any disclaimer, the term of this patent is extended or adjusted under 35 U.S.C. 154(b) by 355 days.

(21) Appl. No.: 10/484,737

(22) PCT Filed: Jul. 24, 2002

(86) PCT No.: PCT/DE02/02718
§ 371 (c)(1),
(2), (4) Date: Aug. 6, 2004

(87) PCT Pub. No.: WO03/011124
PCT Pub. Date: Feb. 13, 2003

(65) Prior Publication Data
US 2005/0014999 A1    Jan. 20, 2005

(30) Foreign Application Priority Data
Jul. 26, 2001 (DE) .................. 101 36 355

(51) Int. Cl.
*A61B 5/103* (2006.01)
(52) U.S. Cl. ............................................ 600/587
(58) Field of Classification Search .............. 600/300, 600/301, 587–595, 500–509, 553–554, 528, 600/552, 483; 606/238; 601/107; 422/82.07
See application file for complete search history.

(56) References Cited

U.S. PATENT DOCUMENTS

| | | | |
|---|---|---|---|
| 4,270,547 A | | 6/1981 | Steffen et al. |
| 4,974,599 A | | 12/1990 | Suzuki |
| 5,657,763 A | * | 8/1997 | Schneider .................. 600/553 |
| 5,699,808 A | * | 12/1997 | John ........................... 600/483 |
| 5,882,303 A | | 3/1999 | Stuessi |
| 5,957,854 A | | 9/1999 | Besson et al. |
| 6,167,290 A | | 12/2000 | Yang et al. |
| 6,228,042 B1 | * | 5/2001 | Dungan ..................... 601/107 |
| 6,360,124 B1 | | 3/2002 | Iwabuchi |
| 6,790,178 B1 | * | 9/2004 | Mault et al. ................ 600/300 |
| 2002/0098120 A1 | * | 7/2002 | Blazewicz et al. ......... 422/82.07 |
| 2003/0055406 A1 | * | 3/2003 | Lebel et al. ................ 604/891.1 |

FOREIGN PATENT DOCUMENTS

DE    40 12 874 A1    9/1991
(Continued)

*Primary Examiner* — Max Hindenburg
*Assistant Examiner* — Fangemonique Smith
(74) *Attorney, Agent, or Firm* — Michael J. Striker

(57) ABSTRACT

The invention lies in the domain of medical technology and relates to a diagnosis and monitoring device for the rapid diagnosis and monitoring of vital parameters of the human or animal body, in particular of the heart and/or lungs, said device being compact, without cables and/or tubes and easy to use for the user. Devices such as a bell (1) comprising a membrane (2) and/or measuring electrodes (4, 5) for receiving and forwarding acoustic and/or electric signals of the body are arranged in a housing with a cross-section that is approximately the size of the palm of a hand and a height of approximately half a hand-width, on the side of a housing that is to be placed on the body. Said devices are connected to a device in the housing, which analyses, filters and stores the signals of the receiving device and to additional devices for visually reproducing the evaluated signals in digital or analogue form using display fields (14, 15, 16, 17) and/or for acoustically reproducing said signals using a loudspeaker (9) located in the housing. The diagnosis and monitoring device also comprises interfaces (10, 11) for connecting external devices and equipment (e.g. computer, earphones, printer). The principal characteristics of the invention are illustrated in FIGS. 1 and 3.

9 Claims, 5 Drawing Sheets

FOREIGN PATENT DOCUMENTS

| | | |
|---|---|---|
| DE | 43 29 898 A1 | 4/1995 |
| WO | 88/05282 | 7/1988 |
| WO | 89/00024 | 1/1989 |
| WO | 96/14014 | 3/1996 |

* cited by examiner

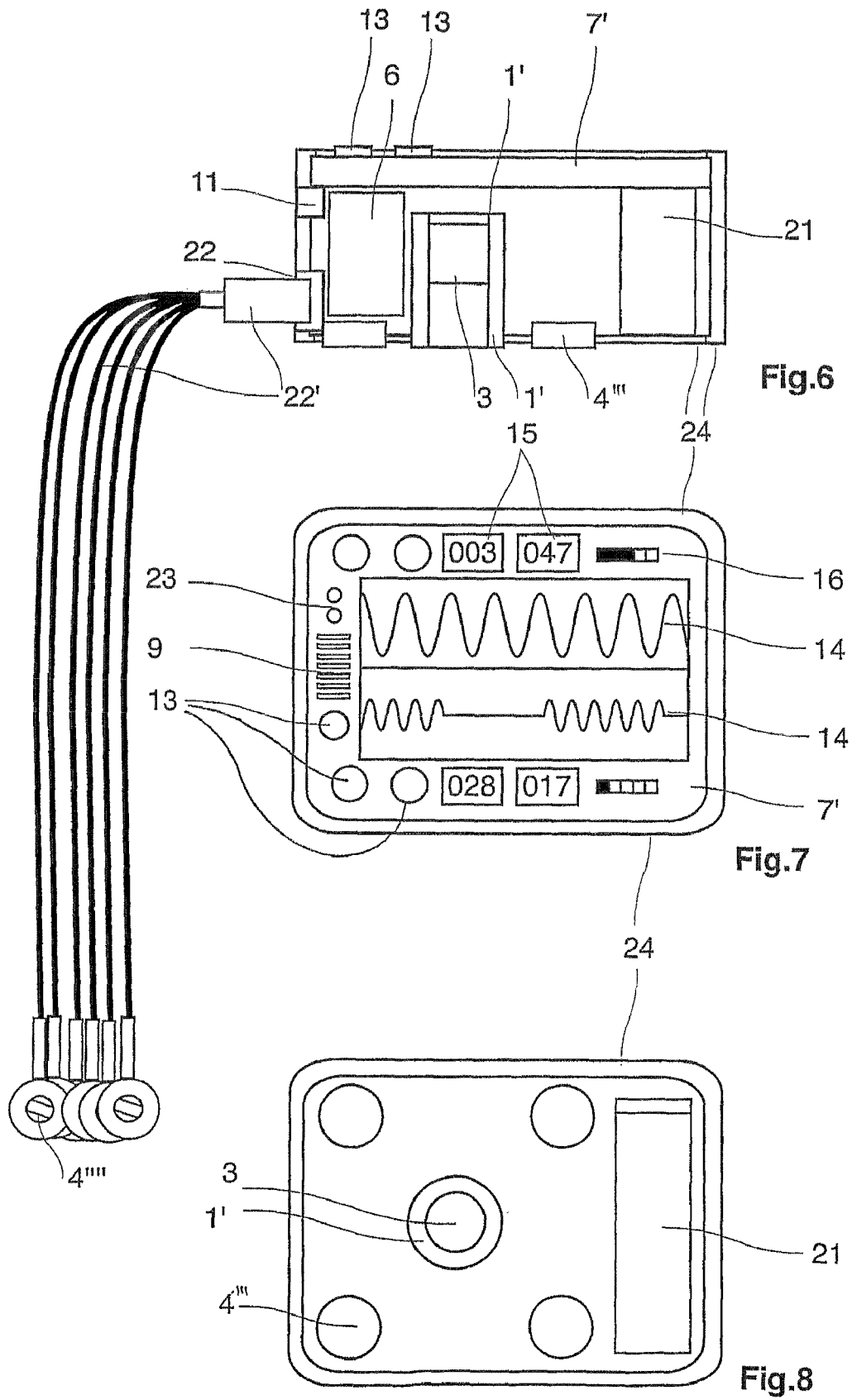

DEVICE FOR VERIFYING AND MONITORING VITAL PARAMETERS OF THE BODY

BACKGROUND OF THE INVENTION

This invention is a device for the examination and monitoring of vital parameters of the human or animal body, in the form of a compact Diagnostic Device, which may be used single-handedly and within easy reach, without the necessity for cables or tubes.

With already known examination and monitoring equipment, several electrodes are attached to the body to be examined, to measure electrical tension fluctuations of the body. Usually, the number of electrodes is increased proportionally to the number of measuring vectors. With most of the well-known equipment, these electrodes are, connected by means of cables to the amplifier units in order to amplify the signals and connect them to separate analysis equipment. This well-known examination and monitoring equipment is, through the cable connections mentioned above and the separate amplifier units and the analysis equipment and especially through the dimensions of these components, most disadvantageous. Firstly, the cables cause obstruction the person being examined. But above all, the doctors are hindered the most, as the equipment is fixed in its location to each person being examined and can not be readily taken by the doctor and, in a short time, be used for other patients.

A cable-free diagnosis and monitoring unit is known from DE 43 29 898 A1. The electrical cable connection of the electrodes to the analysis station, can be here be omitted, as the electrodes attached to the body being examined are equipped with sender units and aerials, through which they are in wireless contact with the analysis station, which receives the recorded signals. The analysis station also has receptor units and aerials. From this publication, it is known that, positioned in one electrode casing are a number of electrode pins, for the recording of electrical potential fluctuations on various points with different vectors. This diagnosis and monitoring equipment, however still has major disadvantages. It is technically too complicated and too expensive, through the necessary transmitters, receivers, detectors, coding and encoding units and more. The relatively large electrodes, by their design, have to be removable, but permanently fixed to the body, whilst for the examination of different body areas separate electrodes, also with the necessary transmitters and receivers are required. Furthermore, the relatively large analysis station is in a separate room, which is a major disadvantage, especially as it contains the display, data storage and alarm units. It is, therefore not always accessible and viewable by the examining technician and especially by the doctor, as the unit is not transportable. A final, major disadvantage is that only a few examination functions are integrated into the device, in particular, no listening with stethoscope (Auskultation) is possible, nor any percussion, no measuring of oxygen saturation of the blood and of the time taken for recapillarisation.

Also known from DE 40 12 874 C2, is a blood pressure measuring device with long-term ECG measuring units, which can be carried on the body. The part of the equipment necessary for the automatic taking of the blood pressure, including the cuff and pump, as well as the analysis and control switches, are combined in one system. This device is especially laid out for the automatic measurement of long-term ECG and blood pressure, and its main task is to take blood pressure measurements in connection with ECG-fluctuations. Because of the required cuff and pump necessary to operate it, the equipment has to be allocated to a single patient and be worn by him/her. In this device, the electrodes and sensors are connected by means of cables to the long-term ECG measuring equipment.

SUMMARY OF THE INVENTION

The aim of the invention is to avoid the disadvantages of known diagnostic and monitoring equipment, by creating a device for a fast diagnosis of the most important vital parameters of the human and animal body, especially the examination of the heart, and/or the lungs in their expansion, condition and ability to function, as well as the constant monitoring of the person being examined, in such a compact form and without cable and/or tube connections, so that it can be readily carried by the technician, especially the doctor, and used immediately without any connections, as well as, a procedure for measuring of oxygenation and circulation outputs of the human and animal body, using x-ray and applying pressure onto an area of the body, followed by a pressure release.

BRIEF DESCRIPTION OF THE DRAWINGS

FIG. 6 shows: a further version of the Diagnostic Device, viewed in cross-section, from the side, as in FIG. 1, but with a sound cylinder, and an external sensor electrode positioned at the interface to the Diagnostic Device and a firmly integrated monitor/screen;

FIG. 7 shows: the Diagnostic Device as in FIG. 6, viewed from above, with the display and operational area as well as a monitor/screen;

FIG. 8 shows: the Diagnostic Device as in FIG. 6, viewed from below, as in FIG. 2;

DESCRIPTION OF THE PREFERRED EMBODIMENTS

Figure 1:
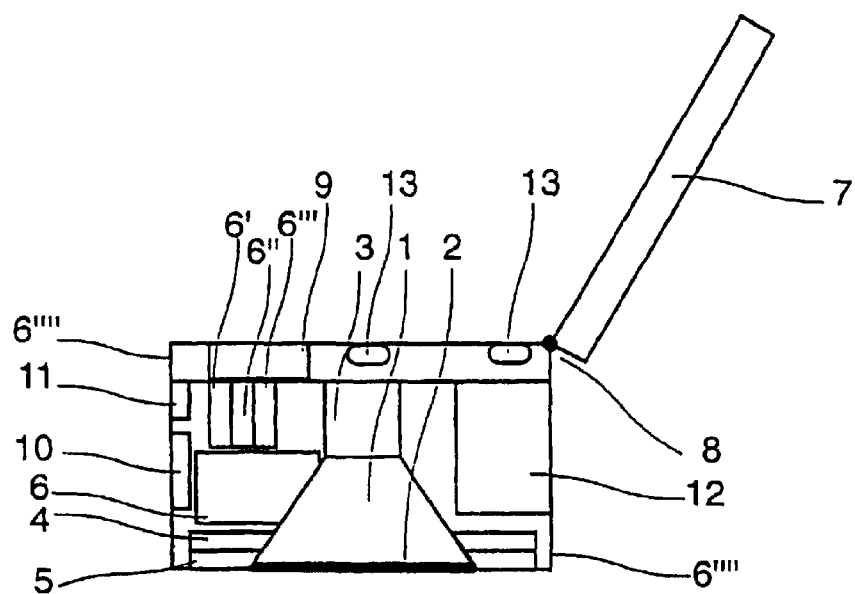
FIG. 1 shows: the device for the diagnosis and monitoring of the vital parameters, viewed in cross-section, from the side.
Figure 2:
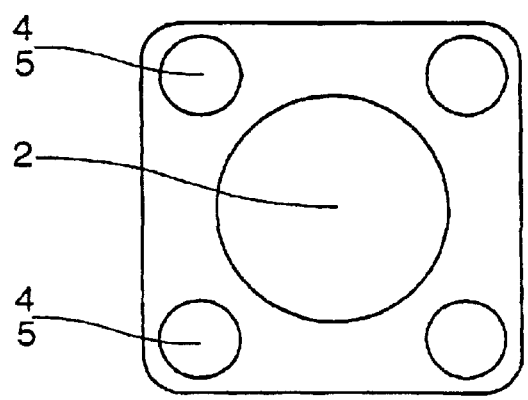
FIG. 2 shows: the Diagnostic Device as in FIG. 1, viewed from the underside, which will be placed on the person to be examined.
Figure 3:
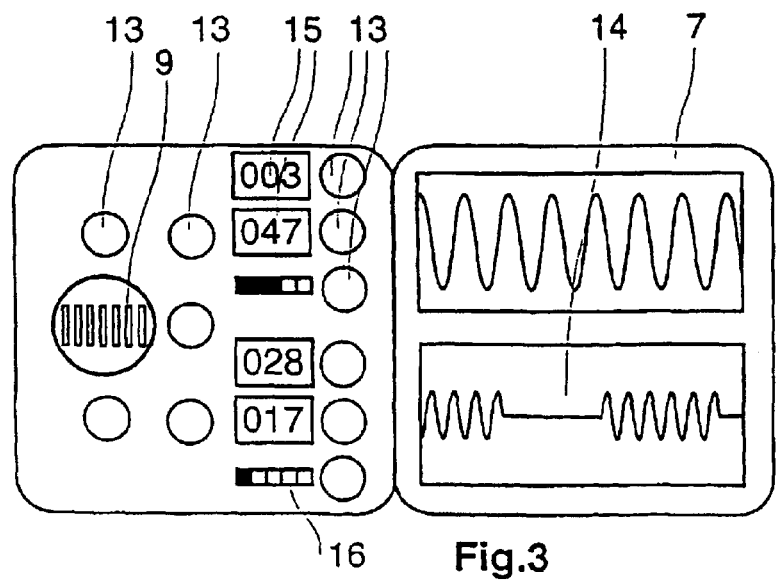
FIG. 3 shows: the Diagnostic Device as in FIG. 1, viewed from above, with monitor screen open, as well as the operational and display unit.

In the described version of the Diagnostic Device in FIG. 1 to 3, are the recording units for the acoustic signals of the body (1, 2, 3) as well as the recording units for the electrical signals, in the form of tension fluctuations and/or of impedance measurements, and/or for temperature measurements, consisting of four measuring electrodes (4) with a receptacle for contact gel (5), placed in the casing; the sound funnel and the measuring electrodes with the contact gel receptacle are pointed towards the person/object being examined, when using the device. The membrane (2) of the sound funnel and the cover for the contact gel receptacle (5) of the measuring electrode (4), are positioned on a horizontal level. On the upper side of the device, is the operational and display area with the operational keys (13), the speaker (9), the digital display areas (15) and the amplitude beam display (16). On the outer rim of the casing of the Diagnostic Device, is a foldable monitor/screen (7), attached with a hinge (8) situated, which shows curve-fields' display (14) and is placed onto the operational and display area through the hinge (8) when not in use. Inserted into the casing of the Diagnostic Device are—but not individually illustrated in the drawings—analogue and digital electronics to amplify/enhance the measurements, to analyze the measurements and to display them. Furthermore, there is an element for data storage inside the casing of the Diagnostic Device. The recording unit for acoustic signals consists of the sound funnel (1), with an attached membrane (2) and the positioned microphone (3). Finally, there is a compartment in the casing for the storage of power supply elements, for example, batteries or rechargeable accumulator (12). As shown schematically in FIG. 1, the Diagnostic Device does additionally have an interface earphones/headphones (10) and for the connection to a computer (11), on an exterior wall of the casing. The microphone (3) of the sound funnel is connected to the speaker (9) in the operational and display area.

Figure 4:
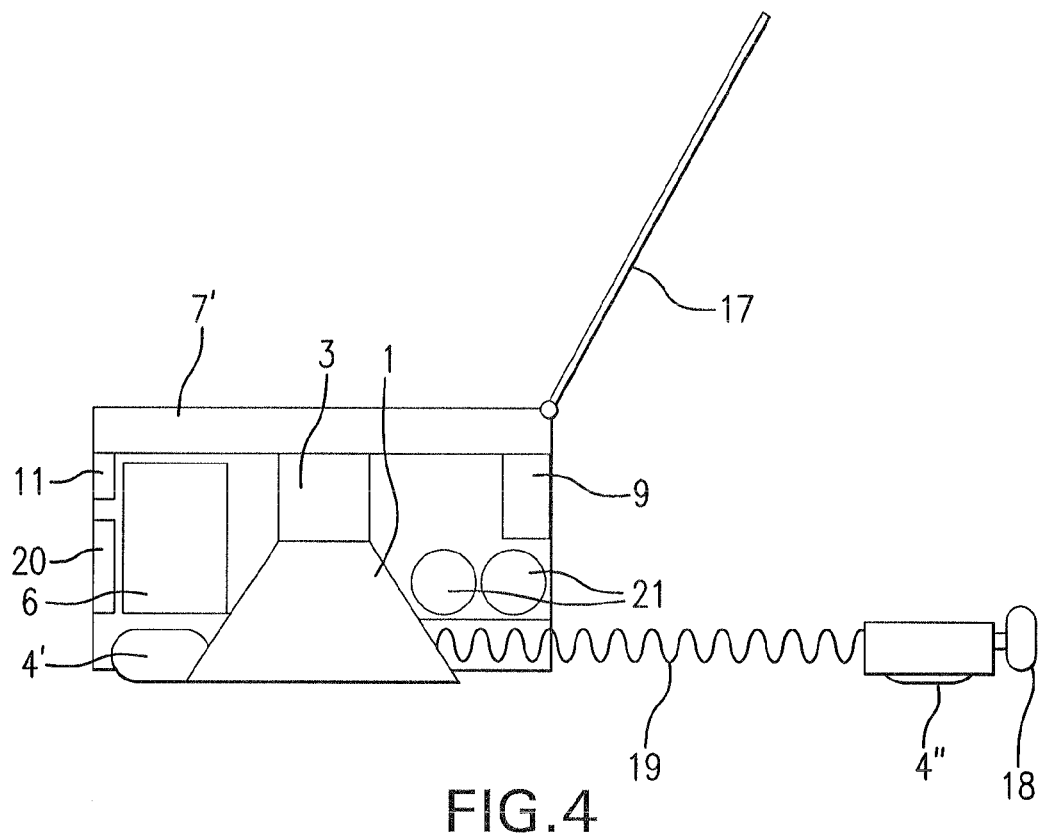
FIG. 4 shows: the Diagnostic Device in an altered version, with a fixed monitor/screen and foldable protective lid, as well as an extractable sensor electrode.
Figure 5:
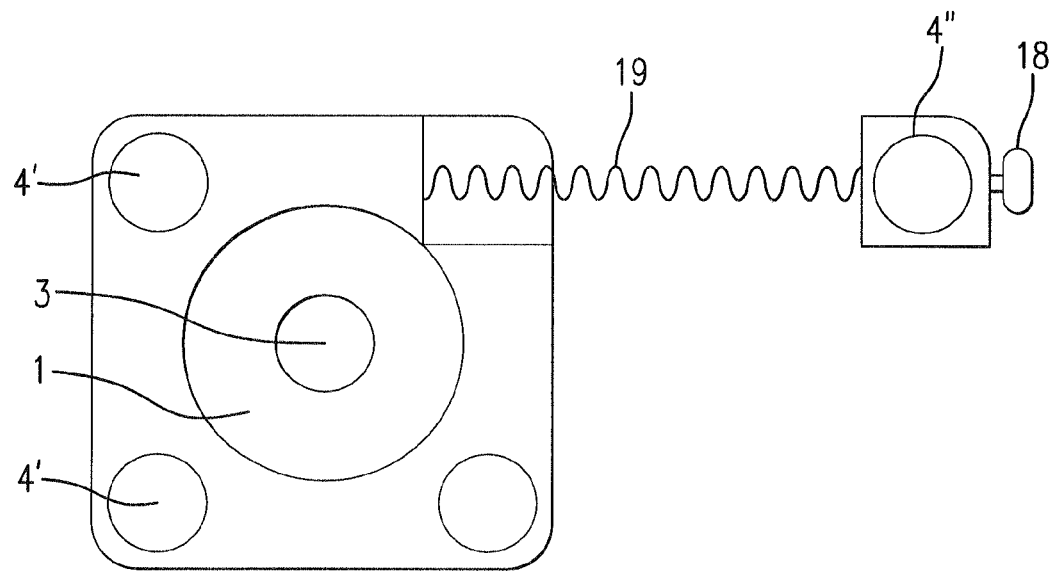
FIG. 5 shows: the Diagnostic Device as in FIG. 4, viewed from below, as in FIG. 2.

In the version in FIGS. 4 and 5 of the Diagnostic Device, instead of the attached, foldable device for the visual reproduction of the electrical signals and/or temperature measurements and the recorded and analyzed by the recording unit, there is a monitor (7), with a curve-fields'display (14) integrated into the operational and display area and developed according to FIG. 7. To protect the operational and display area including the monitor, there is a protective lid (17), which is foldable on the upper side rim of the device. Incidentally, this version of the Diagnostic Device can concur with the version in FIG. 1 to 3. However, in FIG. 4, there are further developments, instead of the measuring electrodes with the contact gel receptacle (5), which are sunken in the casing, measuring electrodes (4') intended, which are on the same level as the sound funnel (1) and the membrane (2) and situated underneath the casing, slightly domed, and usefully protruding.

Further, as is shown in FIGS. 4 and 5, at least one of the electrodes is removable and placed on the bottom of the casing as a measuring electrode (4"), with a connection cable (19) to the Diagnostic Device; it can be positioned separately from the rest of the unit on an area of the body to be examined on its own or, simultaneously, when using the unit with further measuring electrodes, on a different area of the body. To make using the measuring electrode (4") easier, it has a handle (18). In this version, the speaker (9) is also positioned on a different place on the casing of the Diagnostic Device and, instead of the compartment for the rechargeable accumulator (12), a battery slot (21) is intended. Finally, on the casing, there is, in addition to the computer interface (11) or, in its place, an interface (20) for a printer.

A further version is illustrated in FIGS. 6 and 8. They differ to the examples explained above, mainly in that, instead of the sound funnel (1) with a membrane (2), a sound cylinder (1') is used, which serves at the same time as a fixing for the microphone (3), the microphone being switched on afterwards. An interface (22) is provided by means of a connector plug (22') for the connection of external measuring electrodes (4"") via cables. Finally, instead of the measuring electrode (4'), which can be used here, domed measuring electrodes (4''') have been used. The operating and display area with the integrated monitor/screen is also set out according to FIG. 7, but can also be set out as in FIGS. 1 and 3.

Figures 9, 12:
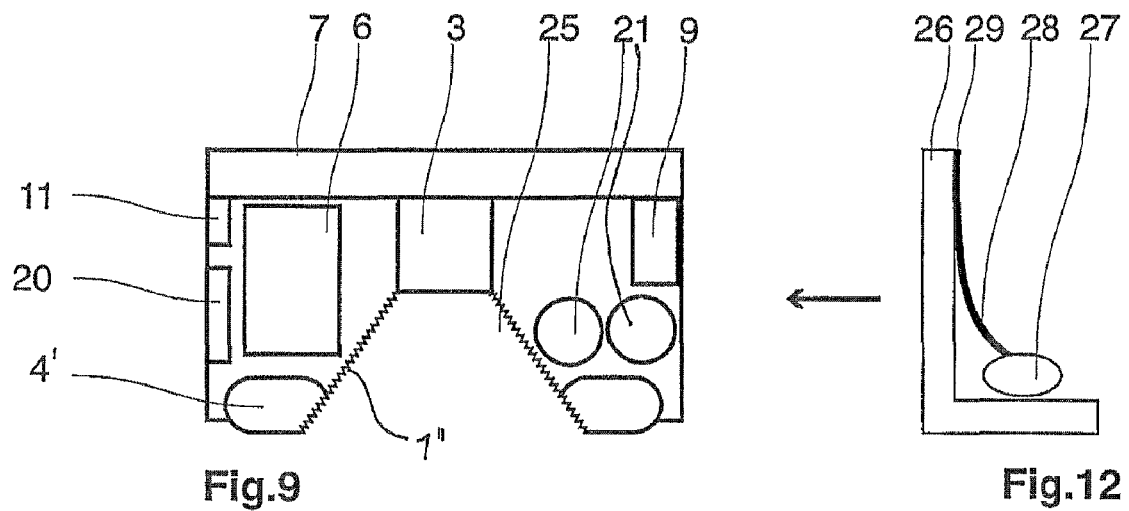
FIG. 9 shows: the Diagnostic Device in a further version, with an exchangeable sound funnel and an exchangeable membrane, for the recording of acoustic signals.
FIG. 12 shows: a sideways attachable percussion module, as a component for the Diagnostic Device, according to FIGS. 1, 4, 6 and 9.
Figure 10:
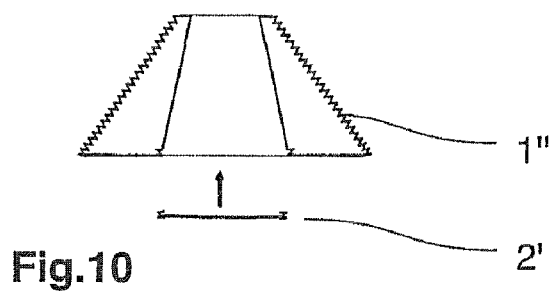
FIG. 10 shows: a detail of FIG. 9; a sound funnel as well as a membrane, before use.
Figure 11:
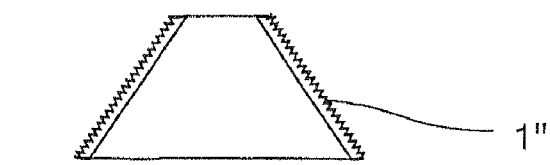
FIG. 11 shows: a detail to FIG. 9; another sound funnel without a membrane.

FIG. 9 to 11 show the Diagnostic Device with a further development of the recording unit for acoustic signals, fitted with an exchangeable sound funnel (1") and exchangeable membrane (2'), whereby the sound funnels used are each connected to the microphone (3) by means of a threaded fitting, a bayonet fixing or in another known way to the casing of the Diagnostic Device.

A percussion module (26 to 29) is shown in FIG. 12. as an additional component, which can be used in all versions of the Diagnostic Device. It consists of an angled elevation (26), preferably made from steel, whose sides are formed by areas facing each other in a right angle. The vertical side corresponds in its height, in the version shown—although not necessarily—to the height of the exterior walls of the Diagnostic Device; the module is firmly connected—but removable—with its outer side flush to one exterior wall of the Diagnostic Device, in such a way, that the horizontal side of the module runs on a horizontal level with the underside of the Diagnostic Device, facing the body part being examined and therefore, also rests on the object being examined. On the vertical side of the angled steel elevation (26), on the inside of the upper area (29), a leaf spring (28) is positioned, which has a knocking mechanism (27) on its lower/bottom end. This knocking mechanism rests, held by a spring, inside the horizontal side of the angled steel elevation (26).

During the examination, by moving the spring (28) with the knocking mechanism (27) by hand, a knocking sound is produced when it springs back onto the horizontal side, which will be resonated by the body or the body part being examined and, thereby, recorded by the acoustic recording device (1, 2, 3; 1', 3'; 1", 2', 3) and passed on for processing.

A further version of the invented Diagnostic Device is shown in FIG. 13 to 16. As is apparent from FIG. 13, here is the acoustic recording device (1, 2, 3) supplemented by the electrical/electronic elements, in which the membrane (2") in front of the sound funnel (1) and facing it, is light reflective on its inside and the light transmitter (41) and the light receiver (41') are facing each other both positioned by the sound funnel (1). In accordance to the movement of the membrane (2"), when placing it on the body being examined—as for example when examining the abdominal wall of a patient with tension conditions—the light reflection, and its different results, are measured through the elements (41, 41') and passed on for analysis, in addition to the acoustic signals. Instead of the light reflecting membrane (2"), in combination with the light transmitter (41) and the light receiver (41'), the membrane (2) can also be connected with a Piezo element or an Eddy current sensor, which converts the movement or position of the membrane, during examination, into electrical/electronic signals. Instead of, or in addition to, these device elements (2", 41, 41'), surface changes can be measured on the body being examined through pressure on the sound funnel (1)—which is resting in the casing and is movable—and this exerted pressure is passed on to a pressure recorder (42, 43).

Figure 13:
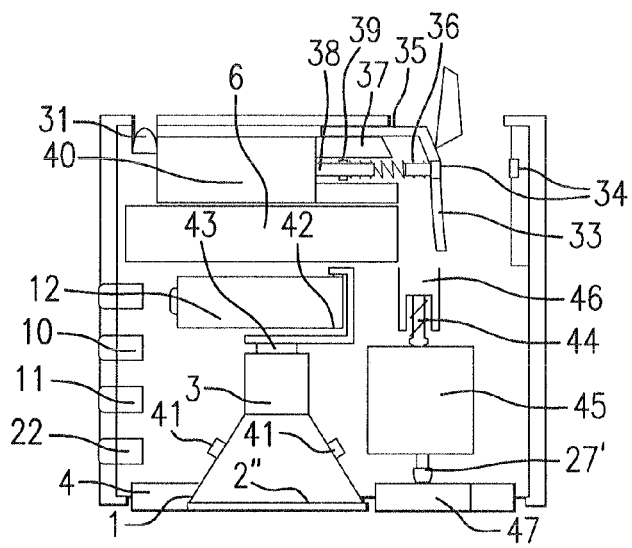
FIG. 13 shows: another version of the Diagnostic Device, viewed in cross-section, with an integrated percussion element containing an electro-magnetically driven tapping device, and, on the upper side, above the operational and display area/monitor, a recording unit with a pressure device for use on inserted body part and a light transmitter/receiver.
Figure 14:
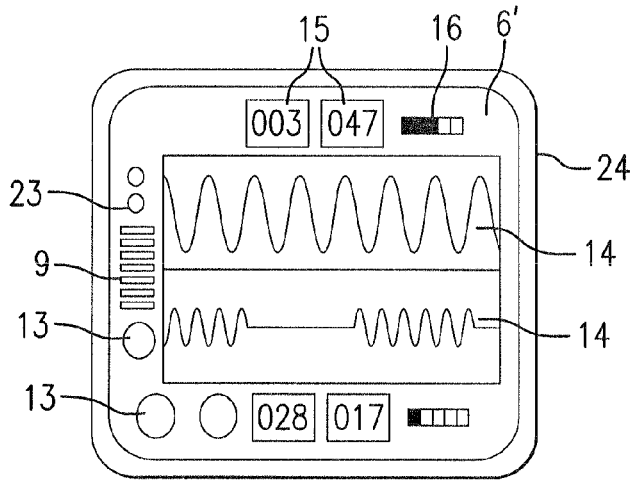
FIG. 14 shows: the operational and display area, with a monitor/screen of the Diagnostic Device as in FIG. 13, viewed from above, after the pressure device and the recording unit have been removed.

In FIG. 13, a sound-producing component (27', 44 to 47) moves into the place of the percussion module, as in FIG. 12, and is integrated in the Diagnostic Device and its casing. The knocking mechanism (27') for producing the sound is driven by an electro-magnetic drive (44, 45, 46) and, in order to produce the sound, knocks onto the striking area (47), which is on the underside of the Diagnostic Device, lying on the same level as the membrane (2, 2") for the acoustic recording unit. This percussion element can also be used in all versions of the Diagnostic Device.

Figure 15:
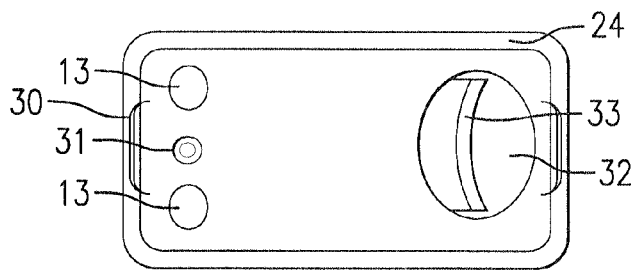
FIG. 15 shows: the Diagnostic Device as in FIG. 13, viewed from above, looking down onto the pressure device.
Figure 16:
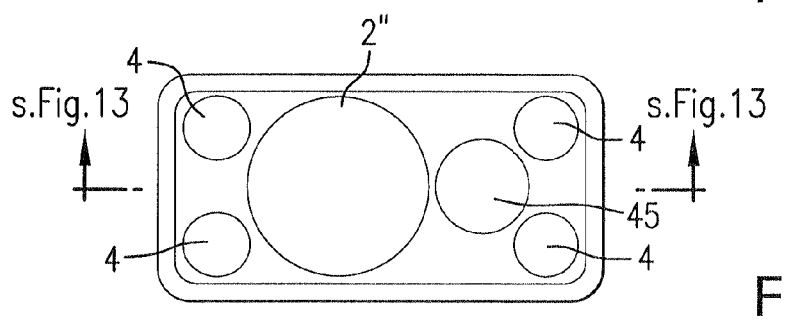
FIG. 16 shows: the Diagnostic Device as in FIG. 13, viewed from below, with measuring electrodes and sound funnel.

In the example in FIG. 13, in addition to measuring the oxygenation and circulation levels of the human or animal body—especially the arterial oxygen saturation of the blood, the arterial capillary and venous blood pressure levels and the recapillarisation time—with the Diagnostic Device described above, there is also a recording unit for ascertaining the light conductance/penetration levels, at the section of the body being examined and the correlation of the light conductance/penetration levels (31 to 40), this unit being folded via a hinge on the side. This recording unit, has an opening for the insertion of a body part, for example a section of a finger, which rests with one side on the exterior wall of the module and on a dish (33) with the opposite side of the body part, which is connected to a pressure device (36 to 40) and is horizontally movable on the guide track (35). The dish (33) is being pushed, by a pressure shaft (38) and the pressure shaft motor (40), against the inserted section of the finger. The force of this pressure is regulated via a regulating element (39) on the pressure shaft (38) and this element measures the amount of the pressure force. Positioned on the dish (33), in the direction of the section of the finger placed upon it, are one or more light transmitters (34), which work together with an appropriate light receiver (34'), on the opposite exterior wall. The results ascertained by the pair of sensors during the x-ray of the body section examined and correlated light conductance/penetration levels, will be passed on as signals to the analyzing electronics of the Diagnostic Device. FIG. 15 shows a fastening device in the form of belt fasteners (30) for the body section being examined, situated on the upper side of the recording unit (33-40). This recording device (33-40) can be used independently of the Diagnostic Devices, as in FIG. 1 to 12, and can, as a separate Diagnostic Device, be used and equipped with a device for electronic analysis/evaluation, filtering and data storage of the supplied signals.

Finally, FIGS. 13 and 15 show a lamp (31), which can be used with all versions of the Diagnostic Device, and can be useful for checking the functioning of the pupils.

The invented device and the procedures carried out with it, make the examination and an extended, comparable overview of the vital parameters of a patient possible—amongst other things with the ECG, blood pressure or circulation levels, oxygenation levels (the oxygen saturation of the blood), the recapillarisation time, the tocography and listening with a stethoscope (Auskultation)—within a compact unit, which can be carried around by the person conducting the examination, or the doctor. It contains all the necessary recording, transmitting, analyzing and data storing devices for such an extensive diagnosis and for the monitoring of the ascertained electrical and acoustic signals of the body or the body parts examined, as well as display areas for the ascertained and analyzed signals. The storage and the optical and acoustic display of the data, make it possible to compare assessments of the measuring results, especially the ECG, as well as heartbeats and heart sounds heard from stethoscope (Auskultation) and percussion, and a side-by-side comparison of measurements can be made, for example by listening with a stethoscope (Auskultation) and with the percussion. The device can be used with a number of patients at any given time and makes it possible, to immediately analyze mechanical, acoustic and electrical occurrences or signals, especially the analysis of the heart and the lung and their functioning. Furthermore, the data storage function (Memory-Funktion) of the device makes it possible to compare the analyses of two occurrences at the same time or of occurrences at different times. Because of this, the device brings major advantages, in comparison to the known diagnostic and monitoring equipment, namely, in the emergency room, in the hospital admission examination departments and to doctors seeing patients in the hospital and also in their surgeries.

The invention claimed is:

1. A device for examination and monitoring of vital parameters, from for example lung and respiration, heart and circulation, of a human or animal body, the device configured as a compact diagnostic device functioning independently of other devices and independently of communication with other devices, adapted to be used single-handedly and within reach of a user without cables, tubes, poking out parts, invasive procedures or implantable parts and comprising a common casing of a size fittable into pockets of a doctor's coat of substantially a size of a palm of a hand with a width and a length of substantially half a hand; devices interacting with the body and devices recording and transmitting one or more signals spontaneously emitted by the body or as a reflex of the interactions with the body all together integrated in said common casing, said recording and transmitting devices including a device performing electronic analysis, filtering and data storage, with intermediate storage of signals supplied by the recording devices; devices providing a parallel playback of a freely definable selection of analyzed signals consisting of devices providing visual playback in digital and analog form, devices providing acoustic playback, and both devices providing visual playback in digital and analog form and devices providing acoustic playback, wherein said body signals recording device includes a multifunctional sensor unit recording electrical voltage fluctuations, impedance measurements and temperature measurements with the same sensor, said body signals recording device including at least two measuring electrodes which are positioned on one level on an underside of said casing for placing over or onto body areas being examined; wherein the multifunctional sensor unit of said body signals recording device also producing, recording and transmitting acoustic signals of different frequency patterns and mechanical strain and elasticity of a body surface and includes a knocking mechanism with an electro-magnetic drive and a striking area so that standardized sound waves are produced and a sound funnel, a membrane and a microphone, said membrane being positioned on an underside of said housing for placing over or onto body areas being examined and said sound funnel is slidable vertically in said casing and thus transfers the strain of the body surface to a pressure recorder, and wherein the multifunctional sensor unit of said recording and transmitting body signals device also recording and transmitting the pulse oxymetry and the arterial capillary and venous blood pressure levels and the recapillarisation time and includes an opening for the insertion of a body part with one side on the exterior wall of the module and with the opposite side of the body part on a dish, and includes a pressure device which is horizontally movable on a guide track, whereby the dish is repulatable—pushable or releasable—by a pressure shaft and a pressure shaft motor against the insertable section of the body part and a pressure is being regulated and measured via a regulating element on the pressure shaft; and the device also includes, on the dish in a direction of the body part section to be inserted, a light transmitter, which works together with a light receiver on an opposite exterior wall of the sensor module and, during this process, this light is being x-rayed and reflected, measured, analyzed and correlated.

2. A device as defined in claim 1, wherein said visual playback of analyzed signals devices include operational and display areas with digital display areas, amplitude beam display, operational keys and a monitor screen with curve-fields display integrated into the operational and display areas and positioned on said casing, said visual playback of analyzed signals devices being configured so that a number of said analyzed signals are recorded at the same time or at different times in a way that a selection of said analyzed signals is displayed in parallel, and that a quantitative analysis of aspects of a single one of said analyzed signals or relations of multiple ones of said analyzed signals is played simultaneously as numbers or beams, said operational and display areas in said monitor screen being fitted to an upper side of said casing so as to face away from a body.

3. A device as defined in claim 1, wherein said acoustic playback device is a speaker with which one or more of the raw signals are acoustically played or sound sequences mark certain aspects of one signal or relations of multiple signals such as marking the heart rate or exceeding an alarm limit, integrated into said casing and positioned on a.side.of said casing so as to face away from a body.

4. A device as defined in claim 1, wherein said acoustic signals recording unit has an exchangeable sound funnel placed in said casing and an exchangeable membrane positioned on said sound funnel.

5. A device as defined in claim 1, wherein said measuring electrodes on the underside of said casing are placed slightly inwards, and each of said measuring electrodes has a receptacle into which a contact substance can be filled.

6. A device as defined in claim 1, wherein one of said measuring electrodes has a slightly domed surface and another of said measuring electrodes have a straight surface.

7. A device as defined in claim 1, wherein said acoustic signals recording unit has an exchangeable sound funnel placed in said casing and an exchangeable membrane positioned on said sound funnel.

8. A device as defined in claim 1, wherein said body signals recording device includes a multifunctional sensor unit recording and transmitting acoustic signals of different frequency patterns and mechanical strain and elasticity of a body surface and includes a sound funnel with a membrane which is light reflective on each side and faces said sound funnel, and a light transmitter and a light receiver facing each other and positioned on said sound funnel for ascertaining different light reflections of a vertical doming of said membrane and transmitting them to an electrical analysis device.

9. A device as defined in claim 8, wherein said membrane is connected to an element selected from the group consisting of a piezo element and an eddy current sensor, which converts a movement or position of said membrane into electrical or electronic signals during an examination process.

* * * * *